United States Patent [19]

Bartmann et al.

[11] 4,258,053

[45] Mar. 24, 1981

[54] THIENYL-PROSTAGLANDINS AND PROCESS FOR THEIR MANUFACTURE

[75] Inventors: Wilhelm Bartmann, Neuenhain; Gerhard Beck, Frankfurt am Main; Dieter-Bernd Reuschling, Butzbach; Karl Seeger, Hofheim; Hermann Teufel, Kelkheim, all of Fed. Rep. of Germany

[73] Assignee: Hoechst Aktiengesellschaft, Frankfurt am Main, Fed. Rep. of Germany

[21] Appl. No.: 136,982

[22] Filed: Apr. 3, 1980

Related U.S. Application Data

[63] Continuation of Ser. No. 692,272, Jun. 3, 1976, abandoned.

[30] Foreign Application Priority Data

Jun. 5, 1975 [DE] Fed. Rep. of Germany ....... 2524955

[51] Int. Cl.$^3$ ................. C07D 333/32; C07C 177/00
[52] U.S. Cl. ...................................... 424/275; 542/426
[58] Field of Search ......................... 424/275; 542/426

[56] References Cited

U.S. PATENT DOCUMENTS

| | | | |
|---|---|---|---|
| 3,931,279 | 1/1976 | Nelson .................. | 542/429 |
| 3,932,289 | 1/1976 | Johnson et al. .......... | 542/429 |
| 3,956,284 | 5/1976 | Hess et al. ............. | 542/429 |
| 3,978,229 | 8/1976 | Matsumoto et al. ........ | 424/275 |
| 4,004,021 | 1/1977 | Bowler et al. ........... | 424/275 |

FOREIGN PATENT DOCUMENTS 2200014  4/1974  France .

*Primary Examiner*—Arthur P. Demers
*Attorney, Agent, or Firm*—Curtis, Morris & Safford

[57] ABSTRACT

The present invention relates to thienyl-prostaglandin derivatives and to a process for their manufacture. The compounds according to the invention have valuable pharmaceutical properties.

3 Claims, No Drawings

THIENYL-PROSTAGLANDINS AND PROCESS FOR THEIR MANUFACTURE

This is a continuation of application Ser. No. 692,272, filed June 3, 1976, now abandoned.

The present invention relates to thienyl-prostaglandins and to a process for their manufacture.

Prostaglandins are a group of natural substances which have been isolated from various animal tissues. They are responsible for a large number of physiological effects in mammals. The natural prostaglandins have a carbon skeleton of generally 20 carbon atoms and differ chiefly in a major or minor content of hydroxyl groups or double bonds in the cyclopentane ring (the structure and action of prostaglandins are described, inter alia, in M. F. Cuthbert "The Prostaglandins, Pharmacological and Therapeutic advances", William Heinemann Medical Books, Ltd., London 1973).

The synthesis of analogues of prostanoic acids which do not occur naturally and in which the large number of pharmacological actions of the natural prostanic acids are differentiated, acquires an increasing importance.

The present invention provides prostanoic acid analogs which do not occur naturally of the general formula I

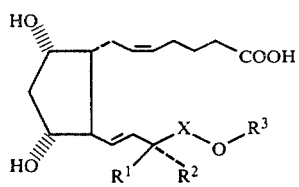

which comprises both the optically active compounds of the natural configuration and the racemic compounds and in which:

- $R^1$ and $R^2$ each is hydrogen or a hydroxyl group, $R^1$ and $R^2$ being different,
- $R^3$ is a α- or β-thienyl radical or a α- or β-thienylmethyl radical which may be substituted 1 to 3 times in the nucleus by halogen, trifluoromethyl and/or alkyl or alkoxy having 1 to 6 carbon atoms each and/or by a phenyl radical which is unsubstituted or substituted 1 to 3 times by halogen, trifluoromethyl and/or alkyl or alkoxy having 1 to 5 carbon atoms, or $R^3$ is a benzo[b]thiophene radical which may be substituted 1 to 3 times by trifluoromethyl, or $R^3$, is a cyclopentano-[b]-thiophene radical or a cyclohexano[b]thiophene radical,
- X is a straight-chain or branched alkylidene or alkylene group having 1 to 7 carbon atoms or a straight-chain or branched alkoxyalkylene group of 2 to 8 carbon atoms, and their physiologically acceptable salts with organic or inorganic bases and their esters with aliphatic, cycloaliphatic or araliphatic alcohols having 1 to 8 carbon atoms.

The invention further relates to a process for the manufacture of the new analogs of prostanoic acids of the formula I, their physiologically acceptable salts with organic and inorganic bases and their esters as well as to pharmaceutical preparations containing these active compounds.

The process is characterized in that
(a) the aldehyde of the formula III

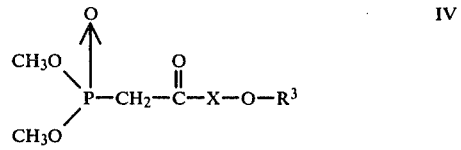

is reacted with a phosphonate of the formula IV

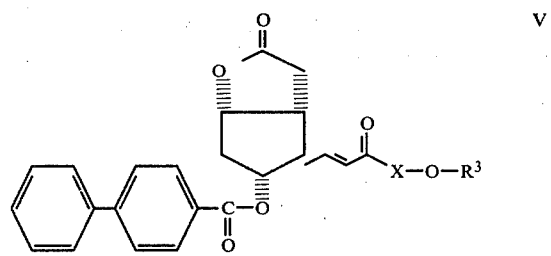

wherein X and $R^3$ are defined as in the formula I, to an unsaturated ketone of the formula V

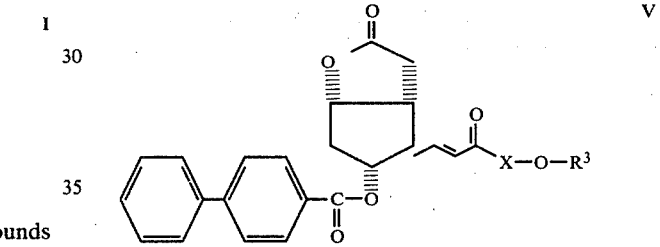

(b) the ketone of the formula V is reduced with a complex metal hydride to the epimer mixture of the alcohols of the formula VI

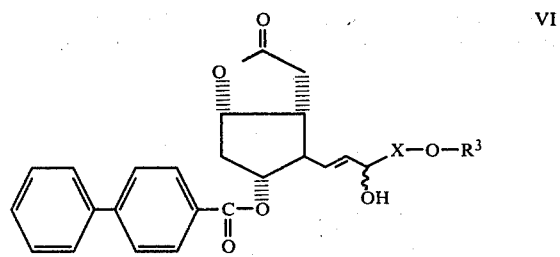

wherein X and $R^3$ are defined as in the formula I, and the epimer mixture so obtained of the alcohols is separated into the S-epimer and the R-epimer optionally subsequently by means of column chromatography, (c) the alcohols (epimer mixtures or pure S— or R— epimers) of the formula VI are converted, at room temperature, as epimer mixture or as S— or R—epimer with an anhydrous alkali metal or alkaline earth metal carbonate in an alcoholic medium into a diol of the formula VII

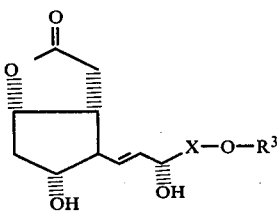

VII wherein X and R³ are defined as in formula I, (d) the diol so obtained of the formula VII is converted by addition of 2,3-dihydropyrane in the presence of acid catalysts into a di-tetra-hydropyranyl ether of the formula VIII

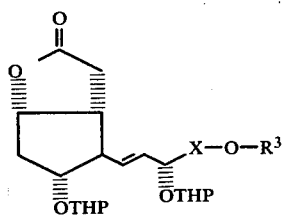

VIII wherein X and R³ are defined as in formula I, (e) the di-tetrahydropyranyl ether so obtained of the formula VIII is reduced with a complex aluminum hydride in an aprotic solvent to a lactol of the formula IX

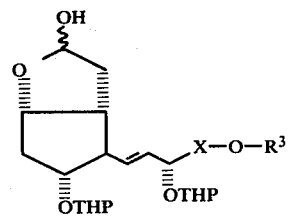

IX wherein X and R³ are defined as in formula I, (f) the lactol of the formula IX is reacted with the ylide of 4-carboxy-butyl-triphenylphosphonium bromide in a solution of sodium hydride in dimethyl sulfoxide in an inert atmosphere to an acid of the formula X

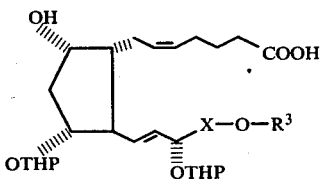

X wherein X and R³ are defined as in the formula I and (g) the tetrahydropyranyl protective groups in a compound of the formula X are split off by acid hydrolysis and the compound of the formula I so obtained is optionally converted into a physiologically acceptable salt or an alkyl ester.

Of the radicals mentioned for the substituent X, the methylene, the ethylene, the ethylidene as well as the isomeric isopropylene and methoxyethylene groups possible with regard to the bonds are preferred.

Of the groups mentioned for the substituent R³ are preferred the unsubstituted α- or β-thienyl as well as α- or β-thienylmethyl radicals, further α- or β-thienyl and thienylmethyl radicals which are substituted 1 to 3 times by chlorine, trifluoromethyl and/or methoxyl or methyl. Preferred substitutents of the thiophene radicals are also the phenyl group which is unsubstituted or substituted respectively 1 to 3 times by halogen, especially chlorine, by trifluoromethyl groups and/or by alkoxy having 1 to 3 carbon atoms, especially methoxyl or methyl. Preferred substituents R³ are furthermore the benzo[b]thienyl radical which is unsubstituted or substituted 1 to 3 times by the trifluoromethyl group, the cyclopentano[b]thienyl and the cyclohexano[b]thienyl radical.

The following groups for R³ are especially preferred: 3-thienyl, 2-(2'-methyl)-thienyl, 2-(3-methoxy)-thienyl, 2-(3-methoxy)-thienylmethyl, 3-(2-ethoxymethyl)-thienyl,
3-(2-methoxymethyl)-thienyl, 2-(3-chloro)-thienyl, 2-(2-thienyloxy)-ethyl, 3-(2',3'-dimethyl)-thienyl, 3-(3'-trifluoromethyl)-thienyl, 3-(3'-chloro)-thienyl, 3-(3'-methyl)-thienyl, 3-(3'-phenyl)-thienyl, 3-(2'(3-trifluoromethyl-phenyl))-thienyl, 3-(2'(4-methoxyphenyl))-thienyl, 3-(2'-methyl)-thienyl, 5-trifluoromethyl-3-benzo[b]thienyl, 3-cyclopentano[b]thienyl, 2-cyclopentano[b]thienyl, 2-cyclohexano[b]thienyl.

The process according to the invention starts from the aldehyde of the formula III which is prepared according to German Offenlegungsschrift DT-OS No. 24 16 193 from the primary bicyclic alcohol of the formula II

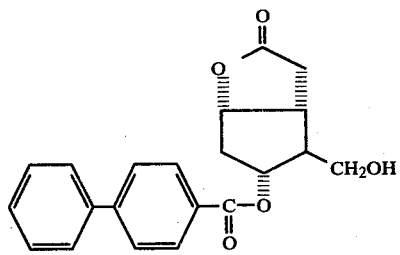

II by oxidation with an oxidizing agent, for example with a complex of thioanisol and chlorine or the complex compound of CrO₃ and pyridine in an aprotic solvent at temperatures ranging between −50° C. and room temperature, preferably −30° C. and −5° C. in an inert atmosphere. Suitable solvents are, in this case, for example aromatic hydrocarbons, such as benzene or toluene or for example chlorinated aliphatic hydrocarbons, such as carbon tetrachloride.

The aldehyde of the formula III is reacted by the method of Horner, Wittig and Emmons with a phosphonic acid ester of the formula IV to give an unsaturated ketone of the formula V; a preferred embodiment of the reaction comprising preparing the sodium salt of the phosphonic acid ester by means of sodium hydride in glycol dimethyl ether, then adding the aldehyde of the formula III and allowing the reaction to take place at room temperature for 2 to 6 hours.

A phosphonic acid ester of the formula IV may be prepared by reacting an ester of the formula R³—OX—CO₂—alkyl in the presence of excess butyl-lithium and methylphosphonic acid dimethyl ester (for example, by the method of Corey, J. Am. Chem. Soc. 88, 5654 (1966)).

The epimeric mixture of alcohols of the formula VI is obtained from the ketone of the formula V by reduction with a complex metal hydride, preferably with an alkali metal boranate or zinc boranate in ethereal solution, preferably at a temperature within the range of from 0° C. to room temperature. The zinc boranate is preferably prepared in situ from zinc chloride and sodium borohydride in absolute ethereal solution.

The alcohols of the formula VI are particularly suitable for separation into the S-epimers and R-epimers, preferably by means of column chromatography on silica gel, but the further reactions can also be carried out with the mixture of epimers and the separation of the epimers can be carried out at the stage of the end product.

The subsequent hydrolytic splitting of the p-phenylbenzoyl group of the alcohol of the formula VI is carried out in an alcoholic medium with the aid of an alkali metal carbonate or an alkaline earth metal carbonate. An advantageous embodiment consists of treating the alcohol or the corresponding mixture of epimers in absolute methanol at room temperature with anhydrous potassium carbonate, a diol of the formula VII being formed.

The di-tetrahydropyranyl ether of the formula VIII is prepared, generally in an ethereal or benzene solution of the alcohols of the formula VII, in the presence of a customary acid catalyst, such as, for example, toluenesulfonic acid.

The resulting compound of the formula VIII is reduced to a lactol of the formula IX by means of a complex aluminum hydride in an aprotic solvent. It is preferable to use diisobutyl-aluminum hydride in toluene at −60° C. to −70° C.

The resulting lactone of the formula IX can be reacted by the method of Wittig, without further purification, to give a carboxylic acid of the formula X. The preferred embodiment of this process follows the instructions given in J. Org. Chem. 28, 1128 (1963).

The protective ether groups in a compound of the formula X are split off by mild acid hydrolysis of the tetrahydropyranyl ether groups by means of an aqueous organic acid, preferably in 2% strength aqueous-alcoholic oxalic acid solution at 20° C. to 50° C., or by heating for 1 to 2 hours in 60% to 70% strength acetic acid at 40° C., a carboxylic acid of the formula I being formed.

If separation of epimers has not been carried out at the stage of the alcohols of the formula VI, a separation of the 15-S-epimer from the 15-R-epimer is preferably carried out after formation of a compound of the formula I. In this process, the separation is preferably carried out on silica gel (Merck, 70–230 mesh), the 15-S-epimer usually being eluted after the 15-R-epimer.

A suitable eluting agent for the separation by column chromatography of the compounds of the formula I is a mixture of chloroform and glacial acetic acid in the ratio of 97.5:2.5.

The compounds of the formula I may optionally be converted according to usual methods into physiologically acceptable salts or esters.

In a manner analogous to that described in the following Examples the following preferred compounds may be prepared:

9S,11S,15-Trihydroxy-16-(3-thienyloxy)-5-cis-13-transtetranor-prostadienoic acid
9S,11S,15-Trihydroxy-16-methyl,16-(3-thienyloxy)-5-cis,13-trans-tetranor-prostadienoic acid
9S,11S,15-Trihydroxy-16,16-dimethyl-16-(3-thienyloxy)-5-cis,13-trans-tetranor-prostadienoic acid
9S,11S,15-Trihydroxy-16-(2-(2'-methyl)-thienyloxy)-5-cis,13-trans-tetranor-prostadienoic acid
9S,11S,15-Trihydroxy-16,16-dimethyl,16-(2-(2'-methyl)-thienyloxy)-5-cis,13-trans-tetranor-prostadienoic acid
9S,11S,15-Trihydroxy-16-(2-(3-methoxy)-thienyloxy)-5-cis,13-trans,-tetranor-prostadienoic acid
9S,11S,15-Trihydroxy-16-(2-(3-methoxy)-thienylmethyloxy)-5-cis,13-trans-tetranor-prostadienoic acid
9S,11S,15-Trihydroxy-16-(3-(2-ethoxymethyl)-thienyloxy)-5-cis,13-trans-tetranor-prostadienoic acid
9S,11S,15-Trihydroxy-16-(3-(2-methoxymethyl)-thienyloxy)-5-cis,13-trans-tetranor-prostadienoic acid
9S,11S,15-Trihydroxy-17-(2-(3-chlor)-thienyloxy)-5-cis,13-trans-trinor-prostadienoic acid
9S,11S,15-Trihydroxy-16-(2-(2-thienyloxy)-ethoxy)-5-cis,13-trans-tetranor-prostadienoic acid
9S,11S,15-Trihydroxy-16-(3-(2',3'-dimethyl)-thienyloxy)-5-cis,13-trans-tetranor-prostadienoic acid
9S,11S,15-Trihydroxy-16-(3-(3'-trifluormethyl)-thienyloxy)-5-cis,13-trans-tetranor-prostadienoic acid
9S,11S,15-Trihydroxy-16-(3-(3'-chlor)-thienyloxy)-5-cis,13-trans-tetranor-prostadienoic acid
9S,11S,15-Trihydroxy-16-ethyl-16-(3-(3'-methyl)-thienyloxy)-5-cis,13-trans-tetranor-prostadienoic acid
9S,11S,15-Trihydroxy-16-(3-(3'-phenyl)-thienyloxy)-5-cis,13-trans-tetranor-prostadienoic acid
9S,11S,15-Trihydroxy-16-(3-(3'-(3''-chlor-phenyl))-thienyloxy)-5-cis,13-trans-tetranor-prostadienoic acid
9S,11S,15-Trihydroxy-16-(3-(2'-(3''-trifluormethyl-phenyl))-thienyloxy)-5-cis,13-trans-tetranor-prostadienoic acid
9S,11S,15-Trihydroxy-16-(3-(2'-(4''-methoxy-phenyl))-thienyloxy)-5-cis,13-trans-tetranor-prostadienoic acid
9S,11S,15-Trihydroxy-16-(3-(2'-methyl)-thienyloxy)-5-cis,13-trans-tetranor-prostadienoic acid
9S,11S,15-Trihydroxy-16-(4-methoxy)-3-benzo[b]-thienyloxy)-5-cis,13-trans-tetranor-prostadienoic acid
9S,11S,15-Trihydroxy-16-(5-trifluoromethyl)-3-benzo[b]thienyloxy)-5-cis,13-trans-tetranor-prostadienoic acid
9S,11S,15-Trihydroxy-16-(5-chlor)-3-benzo[b]-thienyloxy)-5-cis,13-trans-tetranor-prostadienoic acid
9S,11S,15-Trihydroxy-16-(3-cyclopentano[b]thienyloxy)-5-cis,13-trans-tetranor-prostadienoic acid
9S,11S,15-Trihydroxy-16-(2-cyclopentano[b]thienyloxy)-5-cis,13-trans-tetranor-prostadienoic acid
9S,11S,15-Trihydroxy-16-(2-cyclohexano[b]thienyloxy)-5-cis,13-trans-tetranor-prostadienoic acid The compounds of the invention of the formula I are analogs of prostanoic acids which do not occur naturally and which can be used as medicaments by virtue of their pharmacological effects.

The natural prostaglandins $PGE_{1\alpha}$, $PGE_{2\alpha}$ or $PGA_2$ have the disadvantage that they are so quickly deactivated in a living body that their pharmacological action cannot be maintained for the time required for therapy.

In contrast to this, the compounds of the invention are distinguished by a longer duration of action and a stronger effect.

The compounds of the invention have a hypotensive and diuretic action, and may be used as abortifacients and contraceptives, as agents for inhibiting secretion of the gastric juices, and as agents against gastric ulcers and asthma. The compounds of the invention are especially suitable contraceptives for human beings and especially suitable agents for synchronization of the estrus in different animal species.

The compounds of the invention may be used in the form of the free acid, physiologically tolerable inorganic or organic salts, or as esters with an aliphatic, cycloaliphatic or aralphatic alcohol. Examples of suitable salts are benzylammonium, triethanolammonium or morpholine salts and alkali metal salts, and the preferred esters are those with saturated, branched or straight-chain, lower aliphatic alcohols, for example, methyl, ethyl, propyl, butyl or pentyl esters, and benzyl esters.

The acids and salts as well as the esters may be used in the form of aqueous solutions or suspensions, or solutions in pharmacologically suitable organic solvents, for example, monohydric or polyhydric alcohols, dimethyl-sulfoxide or dimethyl formamide. A pharmaceutically suitable polymeric carrier, for example, polyvinylpyrrolidone, may also be used.

The preparation of the invention may be in a form suitable for administration, for example, infusion solutions or injection solutions, tablets, as well as preparation which can be applied locally, for example, creams, emulsions, suppositories and aerosols.

The preparations of the invention may comprise compounds of the formula I, salts or esters thereof, as the only active substance, or may also comprise one or more other pharmacologically active substances, for example, diuretics or antidiabetics.

The single dose to be administered to animals, especially to cattle, horses or sheep is 0.05 to 50 mg, preferably 0.5 to 30 mg. The daily dose is 0.1 to 100 mg, preferably 1 to 60 mg. For human beings, infusion solutions are especially suitable. The dose is, for example, 0.2 to 0.5 mg per 2 hours.

The compounds of the formulae V, VI, VII, VIII, IX and X are intermediate products for the synthesis of the compounds according to the invention, of the formula I.

The following Examples illustrate the invention:

MANUFACTURE OF THE STARTING COMPOUND

Synthesis of 2-oxa-3-oxo-6syn-formyl-7-anti-p-biphenyl-carboxy-cis-bi-cyclo[3,3,0]octane (III)

1.34 l of a solution of 21.3 g of $Cl_2$ in 1.5 l of absolute $CCl_4$ were introduced, under argon, into a 2 l four-necked flask and were cooled to $-10°$ C., and 33.3 g of thianisole were added dropwise, a white precipitate being thrown down.

After the addition is complete, the mixture was cooled to $-20°$ C. and stirred for 30 minutes. Meanwhile, a solution of 30 g of lactone-alcohol (II) in at most 300 ml of absolute $CH_2Cl_2$ was prepared. This solution was added dropwise rapidly at $-20°$ C. and the mixture was subsequently stirred for 2-3 hours at $-20°$ C. 54.3 ml of triethyl amine dissolved in 50 ml of absolute $CH_2Cl_2$ were then added dropwise slowly over the course of 1 hour, it being permissible for the temperature to rise to $-5°$ C. towards the end of the dropwise addition.

The reaction mixture was then poured into an ice cooled solution of 600 ml of 15 strength HCl and 1.5 l of diisopropyl ether. The white precipitate of 24 g which was thrown down was filtered off on as large a filter as possible and was washed with ether. The filtrate was poured into a separating funnel and the organic phase was separated off, dried and concentrated, at not more than $+15°$ C., to a volume of approx. 750 ml.

After cooling well, the crystals which have precipitated were filtered off (5 g) and were combined with the filter residue.

Yield: 29 g of white crystals (98%).

Thin layer chromatogram (solvent chloroform-methanol 15:1), $R_f=0.63$.

Nuclear resonance spectrum (in $CDCl_3$), $\delta$-values: 1.9–4.0 multiplet 6H ($-CH_2-$,CH), 5.0–5.34 triplet 1H ($-\underline{CH}-OCO$), 5.65–5.9 multiplet 3H ($-\underline{CH}-OCO$), 7.3–8.2 multiplet 9H(aromatic protons) and 9.8 singlet 1H ($\underline{CH}=O$).

EXAMPLE 1

(a) Synthesis of dimethyl-2-oxo-3-(3-thienyloxy)-propyl-phosphonate (IV a). 89 g of dimethyl methylphosphonate in 250 ml of tetrahydrofurane were cooled under argon to $-70°$ C. 220 ml of a 20% strength n-butyl-lithium solution in hexane were added dropwise with stirring. After 2½ hours, 40.6 g of 3-thienyloxyacetic acid methyl ester in 100 ml of tetrahydrofurane were added dropwise at $-70°$ C. The mixture was then stirred for 2 hours. It was neutralised with 52 ml of glacial acetic acid. The solvent was concentrated in vacuo, the residue was taken up in chloroform and washed with water and the chloroform phase was dried with $MgSO_4$ and concentrated and the residue was distilled in vacuo.

Yield: 70.2 g of a red oil IV a. Column chromatography on silica gel and toluene-ethyl acetate in ratio 1:1 as eluent yielded in the fractions 90–150 42 g of yellow oil (64% of the theory).

| Elementary Analysis | C | H | P | S |
|---|---|---|---|---|
| Calculated $C_9H_{13}O_5PS$ | 40.9 | 5.0 | 11.7 | 12.1 |
| Found | 41.1 | 5.2 | 11.4 | 11.9 |

Nuclear magnetic resonance (in $CDCl_3$), $\delta$-values: 3.28 doublet 2H ($\underline{CH}_2$-P) J=22 Hz, 3.78 doublet 6H ($OCH_3$), 4.68 singlet 2H ($-OCH_2CO-$), 6.2–7.3 multiplet 3H (thiophene).

(b) Dimethyl-2-oxo-3,3-dimethyl-3-(3-thienyloxy)-propyl-phosphonate (IV b)

On treatment with 220 ml of 20% strength butyl lithium solution in hexane and with 40 g of dimethyl-3-thienyloxyethyl acetate 89 g of dimethyl methylphosphonate gave: 67 g of a red oil. Column chromatography as described under (a) gave 25.1 g of a yellow oil (46% of the theory) in the form of crystals.

Solidification point: 41° C.

| Elementary Analysis: | C | H | P | S |
|---|---|---|---|---|
| Calculated $C_{11}H_{17}O_5PS$ | 45.2 | 5.9 | 10.6 | 11.0 |
| Found | 44.9 | 5.8 | 10.3 | 10.9 |

Nuclear magnetic resonance (in $CDCl_3$) $\delta$-values: 1.5 singlet 6H ($CH_3$), 3.4 doublet 2H ($CH_2-P$) J=22 Hz, 3.8 doublet 6H ($OCH_3$), 6.3–7.3 multiplet 3H (thiophene).

(c) dimethyl-2-oxo-3-(5-methyl-2-thienyloxy)-propyl-phosphonate

Nuclear magnetic resonance (in $CDCl_3$) $\delta$-values:

multiplet at 6.4 ppm (1H, 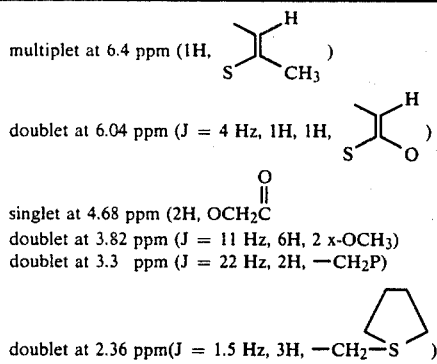)

doublet at 6.04 ppm (J = 4 Hz, 1H, 1H, )

singlet at 4.68 ppm (2H, OCH$_2$C$\overset{\text{O}}{\underset{\|}{}}$)
doublet at 3.82 ppm (J = 11 Hz, 6H, 2 x-OCH$_3$)
doublet at 3.3 ppm (J = 22 Hz, 2H, —CH$_2$P)

doublet at 2.36 ppm(J = 1.5 Hz, 3H, —CH$_2$—S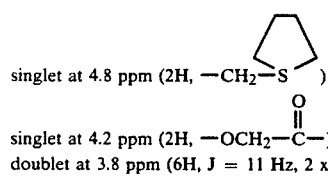)

(d)
dimethyl-2-oxo-3-(2-thienylmethyloxy)-propyl-phosphonate

Nuclear magnetic resonance (in CDCl$_3$) δ-values:

multiplet at 7.3 ppm (1H) thiophene-H
multiplet at 7.0 ppm (2H)

singlet at 4.8 ppm (2H, —CH$_2$—S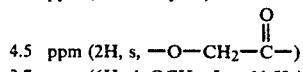)

singlet at 4.2 ppm (2H, —OCH$_2$—$\overset{\text{O}}{\underset{\|}{\text{C}}}$—)
doublet at 3.8 ppm (6H, J = 11 Hz, 2 x-CH$_3$O)
doublet at 3.2 ppm (2H, J = 22 Hz, —CH$_2$P)

(e)
dimethyl-2-oxo-3-(3,5-dimethyl-2-thienyloxy)-propyl-phosphonate $R_f = 0.35$ (ethyl acetate/methanol = 10:1).
Nuclear magnetic resonance (in CDCl$_3$) δ-values:

6.15 ppm (1H, thienyl-H)
4.5 ppm (2H, s, —O—CH$_2$—$\overset{\text{O}}{\underset{\|}{\text{C}}}$—)
3.7 ppm (6H, d, OCH$_3$, J = 11 Hz)
3.2 ppm (2H, d, $\overset{\text{O}}{\underset{\|}{\text{P}}}$—CH$_2$—, J = 22 Hz)
2.28 ppm (3H, d, CH$_3$, J = 1.5 Hz)
2.0 ppm (3H, s, CH$_3$)

(f)
dimethyl-[2-oxo-3-(cyclopentano-[b]thienyl-3-oxy)-n-propyl]-phosphonate

Nuclear magnetic resonance (in CDCl$_3$), δ-values:

—CH$_2$—CH$_2$—CH$_2$— : 2.2–3.0 (6 H, m)
P—CH$_2$—C : 3.3 (2 H, d, J = 23 Hz)
$\|\quad\quad\|$
O$\quad\quad$O
OCH$_3$ : 3.7 (3 H, s), 3.9 (3 H, s)
—C—CH$_2$O— : 4.6 (2 H, s)
$\|$
O
CH (thiophene) : 6.1 (1 H, s)

(g)
dimethyl-[2-oxo-3-(2-phenyl-3-thienyl-3-oxy)-n-propyl]phosphonate

Nuclear magnetic resonance (in CDCl$_3$) δ-values:

P—CH$_2$—C— : 3.3 (2 P, d, J = 23 Hz)
$\|\quad\quad\|$
O$\quad\quad$O
—OCH$_3$ : 3.7 (3 P, s); 3.9 (3 P, s)
C—CH$_2$—O : 4.7 (2 P, s)
$\|$
O
thiophene protons : 6.1 (1 P, d, J = 2 Hz); 7.1 (1 P, d, J = 2 Hz)
phenyl protons : 7.3–7.7 (5 P; m)

(h)
dimethyl-[2-oxo-3-(2-methyl-3-thienyloxy)-n-propyl]-phosphonate

Nuclear magnetic resonance (in CDCl$_3$) δ-values:

2.3  singlet (3 H, CH$_3$)
3.2  doublet (2 H, P—CH$_2$—, J = 22 Hz)
$\quad\quad\quad\quad\quad\quad\quad\|$
$\quad\quad\quad\quad\quad\quad\quad$O
3.8  doublet (6 H, OCH$_3$, J = 11 Hz)
4.6  singlet (2 H, —C—CH$_2$—O—)
$\quad\quad\quad\quad\quad\quad\quad\|$
$\quad\quad\quad\quad\quad\quad\quad$O
6.55 doublet (1 H, thiophene)
6.85 doublet (1 H, thiophene)

(i)
dimethyl-[2-oxo-3-(3-methoxy-2-thienylmethyloxy)-n-propyl]phosphonate

Nuclear magnetic resonance (in CDCl$_3$) δ-values:

| 3.2 | doublet (2 H, P—CH$_2$—, J = 22 Hz)  |
|---|---|
| 3.8 | doublet (6 H, OCH$_3$, J = 11 Hz) |
| 3.83 | singlet (3 H, thiophene-OCH$_3$) |
| 4.1 | singlet (2 H, thiophene-CH$_2$—) |
| 4.6 | singlet (2 H, —C—CH$_2$O—) |
| 6.8 | doublet (1 H, thiophene) |
| 7.2 | doublet (1 H, thiophene). |

EXAMPLE 2a (a) Synthesis of 2-oxa-3-oxy-6(3-oxo-4-(3-thienyloxy)-1-butenyl-7-(4-biphenylcarbonyloxy)-bicyclo 3,3,0 octane (Va)

5.9 g of phosphonate IVa were added dropwise, under argon, over the course of 15 minutes to a suspension of 0.67 g of sodium hydride (80% strength suspension in oil) in 100 ml of absolute 1,2-dimethoxy-ethane. A solution was formed, with evolution of hydrogen. The mixture was stirred for a further 40 minutes and 7.1 g of lactone-aldehyde (III) were then added dropwise over the course of 10 minutes. The mixture was stirred for a further hour, neutralised with glacial acetic acid, clarified with a little animal charcoal, filtered and concentrated in vacuo. The residue was recrystallized from 800 ml of isopropanol. 4.1 g of the desired product were obtained in this way. Yield: 40% of the theory, melting point: 147° C.

| Elementary Analysis: | C | H | S |
|---|---|---|---|
| Calculated $C_{26}H_{24}O_6S$ | 68.8 | 5.0 | 6.6 |
| Found | 70.0 | 5.2 | 6.4 |

Nuclear magnetic resonance (in $CDCl_3$) δ-values: 2.2–3.2 multiplet 6H (—$CH_2$—, —CH—), 4.65 singlet 2H (—$OCH_2CO$—), 4.8–5.6 multiplet 2H (—COO—CH—), 6.2–8.2 multiplet 14H (olefinic protons, aromatic protons). Thin layer chromatogram (developing solvent methylene chloride-ethyl acetate 10:1): $R_f$=0.62.

(b) Synthesis of 2-oxa-3-oxy-6-(3-oxo-4,4-dimethyl-4-(3-thienyloxy-1-butenyl)-7-(4″-biphenylcarbonyloxy)-bicyclo[3.3.0]octane (Vb)

6.5 g of the compound IVb were reacted with 7.0 g of lactone-aldehyde III, analogously to Va. After working up, were obtained, as the compound Vb, 5.6 g of white crystals of melting point 155°–157° C. (49%).

| Elementary Analysis: | C | H | S |
|---|---|---|---|
| Calculated $C_{30}H_{28}O_6S$ | 69.7 | 5.5 | 6.2 |
| Found | 69.9 | 5.6 | 6.3 |

Nuclear magnetic resonance (in $CDCl_3$) δ-values: 1.5 singlet 6H ($CH_3$), 2.2–3.2 multiplet 6H (—$CH_2$—, —CH—) 4.8–6.5 multiplet 2H (—COO—CH), 6.1–8.2 multiplet 14H (olefinic protons, aromatic protons).

Thin layer chromatogram (developing solvent methylene chloride-ethyl acetate 10:1): $R_f$=0.52.

(c) 2-oxa-3-oxo-6(3-oxo-4(5-methyl-2-thienyloxy)-1-butenyl-7-(4-biphenylcarbonyloxy)-bicyclo[3.3.0]octane Vc This compound was prepared in an analogous manner from III and the phosphonate 1c.

Nuclear magnetic resonance (in $CDCl_3$):

doublet at 2.3 ppm (J~2 Hz): 3 H($CH_3$-thiophene)
multiplet at 2.3 to 3.2 ppm: 6 H(—$CH_2$—, CH)
singlet at 4.65 ppm: 2 H(—$OCH_2\overset{O}{\overset{\|}{C}}$)
doublet at 6 ppm, J~4 Hz } (2 thiophene —H)
multiplet at 6.2–6.4 ppm }
doublet 6.4; 6.66: 1 olefinic H
multiplet at 6.7–8.2 ppm: 9 aromatic + 1 olefinic H (d) 2-oxa-3-oxo-6(3-oxo-4-(2-thienylmethyloxy)-1-butenyl-7-(4-biphenyl-carbonyloxy)-bicyclo[3.3.0]octane Vd This compound was prepared from III and the phosphonate 1d.

Nuclear magnetic resonance (in $CDCl_3$, δ-values)

multiplet 2.3–3.1 ppm: 6 H (—$CH_2$, $\overset{\diagup}{\underset{\diagdown}{CH}}$)

-continued singlet 4.2 ppm: 2 H ($OCH_2\overset{O}{\overset{\|}{C}}$—)
singlet 4.75 ppm: 2 H ($OCH_2$-thiophene)
multiplet 4.9–5.5 ppm: 2 H (—CH—$O\overset{O}{\overset{\|}{C}}$—)
doublet 6.30; 6.55
double doublet 7.1 to 6.7 } (2 olefinic H)
multiplet at 6.9–8.2: 9 aromatic + 3 thiophene-H

EXAMPLE 3a

Synthesis of 2-oxa-3-oxy-6-(3-hydroxy-4-(3-thienyloxy)-1-butenyl)-7-(4-biphenylcarbonyloxy)-bicyclo[3.3.0]octane VI 3.5 g of the compound Va were dissolved in 45 ml of 1,2-dimethoxy-ethane. 30 ml of 0.5-molar solution of zinc boronhydride (prepared as follows: 2.8 g of zinc chloride were suspended in 45 ml of 1,2-dimethoxy ether and 1.52 g of sodium borohydride were added with cooling and stirring and the mixture was stirred for 2 hour and quickly filtered from undissolved matter under argon) were added at 0° C. The mixture was stirred for 2½ hours at room temperature. Excess reagent was then decomposed by means of glacial acetic acid at 0° C. The desired product was extracted with ethyl acetate-water. The organic phase was dried with $MgSO_4$, filtered and concentrated in vacuo. The yield of the compound VIa was 3.4 g of a colorless oil (98%).

The 15-S and 15-R-epimers can be separated easily by column chromatography with pure diethyl ether. $R_f$ values for the 15-S epimer in the thin layer chromatogram (ether)=0.28, $R_f$-value for the 15-R epimer=0.19.

Absorption in the infrared spectrum (without solvent): 3455 (OH-band), 2,920, 1,744 (lactone-carbonyl), 1,720 (estercarbonyl).

(b) 2-oxa-3-oxo-6-(3-hydroxy-4-(5-methyl-3-thienyloxy)-1-butenyl)-7-(4-biphenylcarbonyloxy)-bicyclo(3.3.0)octane VIb Nuclear magnetic resonance (in $CDCl_3$), δ-values:

doublet at 2.3 ppm, J~2Hz: 3 H ($CH_3$-thiophene)
multiplet at 2.3 to 3.2 ppm: 7 H (—$CH_2$—, $\overset{\diagup}{\underset{\diagdown}{CH}}$, OH)

multiplet at 3.8 to 4.7 ppm: 3 H (—$\underset{\underset{OH}{|}}{CH}$—$CH_2$—O)

multiplet at 4.8 to 5.5 ppm: 2H (CH—OCO)
multiplet at 5.6–5.9 ppm: 2 H (olefinic H)
doublet at 6.0 ppm, J~4 Hz
(2-thiophene-H)
multiplet at 6.2–6.4 ppm
multiplet at 7.2 to 8.2 ppm: 9 aromatic protons.

(c)

2-oxa-3-oxo-6-(3-hydroxy-4-(2-thienylmethyloxy)-1-butenyl)-7-(4-biphenylcarbonyloxy)-bicyclo(3.3.0)-octane VIc ---
multiplet at 2.0–3.3 ppm: 7 H (—CH$_2$—, CH—, OH)
multiplet at 3.4–4.2 ppm: 3 H (CH—CH$_2$—O)
$\quad\quad\quad\quad\quad\quad\quad\quad\quad\quad\quad$ |
$\quad\quad\quad\quad\quad\quad\quad\quad\quad\quad\quad$ OH
singlet at 4.75 ppm: 2 H (OCH$_2$-thiophene)
multiplet at 4.9–5.5 ppm: 2H (CH—OC—)
$\quad\quad\quad\quad\quad\quad\quad\quad\quad\quad\quad\quad\quad$ ‖
$\quad\quad\quad\quad\quad\quad\quad\quad\quad\quad\quad\quad\quad$ O
multiplet at 5.6–5.9 ppm: 2 olefinic H
multiplet at 6.9–8.2 ppm: 12 aromatic H

---

EXAMPLE 4a

Synthesis of 2-oxa-3-oxy-6(3-hydroxy-4-(3-thienyloxy)-1-butenyl)-7-hydroxy-bicyclo[3.3.0]octane VII 3.25 g of the compound VIa were dissolved in 30 ml of absolute methanol, 1.05 g of very finely powdered potassium carbonate were then added at room temperature and the mixture was stirred under argon for 2½ hours. In the course thereof, a crystalline precipitate of p-diphenylcarboxylic acid methyl ester was thrown down. The mixture was acidified with 1 N hydrochloric acid to pH 2 while cooling with ice, the p-diphenylcarboxylic acid methyl ester was filtered off and the filtrate was treated with ethyl acetate-water. After the extraction, the organic phase was separated off and dried with MgSO$_4$ and the solvent was removed in vacuo. The yield of the compound VII was 1.86 g of a colorless oil (91%).

Thin layer chromatogram (developer solution: methanol-chloroform=1:4): phosphomolybdic acid used as spray reagent: R$_f$=0.75.

(b)

2-oxa-3-oxo-6-(3-hydroxy-4-(5-methyl-2-thienyloxy-1-butenyl)-7-hydroxy-bicyclo(3.3.0)octane VIIb Nuclear magnetic resonance:

---
doublet at 2.3 ppm (J∼2 Hz): 3H (CH$_3$-thiophene)
multiplet at 2.2–3.2 ppm: 8H (—CH$_2$—, CH—, OH)
multiplet at 3.6 to 4.6 ppm: 4H (CH$_2$O—, CH—O)
multiplet at 4.7–5.1 ppm: 1H (CH—OC—)
$\quad\quad\quad\quad\quad\quad\quad\quad\quad\quad\quad\quad$ ‖
$\quad\quad\quad\quad\quad\quad\quad\quad\quad\quad\quad\quad$ O
multiplet at 5.5–5.7: 2-vinyl-H
doublet at 6.0 ppm, J∼4Hz $\}$ 3-thiophene-H
multiplet at 6.3–6.4 ppm

---

(c)

2-oxa-3-oxo-6(3-hydroxy-4-(2-thienylmethyloxy)-1-butenyl-7-hydroxy-bicyclo(3.3.0)octane VIIc Nuclear magnetic resonance:

---
multiplet at 2.0–3.3 ppm: 8H (CH$_2$, CH, OH)
multiplet at 3.3–4.3 ppm: 4H (—CH,—CH$_2$O—, CHOH)
$\quad\quad\quad\quad\quad\quad\quad\quad\quad\quad\quad$ |
$\quad\quad\quad\quad\quad\quad\quad\quad\quad\quad\quad$ OH
singlet at 4.75 ppm (OCH$_2$-thiophene)
multiplet at 4.7–5.1 ppm: 1H (CH—OC)
$\quad\quad\quad\quad\quad\quad\quad\quad\quad\quad\quad\quad$ ‖
$\quad\quad\quad\quad\quad\quad\quad\quad\quad\quad\quad\quad$ O
multiplet at 5.7–5.3 ppm: 2 olefinic H
multiplet at 6.8–7.1 $\}$ 3 thiophene-H
multiplet at 7.1–7.4

---

EXAMPLE 5a

Synthesis of 2-oxa-3-oxy-6(3-tetrahydropyranyloxy-4-(3-thienyloxy)-1-butenyl)-7-tetrahydropyranyloxy-bicyclo[3.3.0]octane (VIIIa)

1.86 g of the compound VIIa were dissolved in 50 ml of absolute methylene chloride and 6.3 g of 2,3-dihydropyrane and 1 ml of 0.5% strength solution of p-toluenesulfonic acid in methylene chloride were then added. The mixture was stirred for 3 hours at room temperature and ethyl acetate was then added, followed by saturated sodium bicarbonate solution. The organic phase was separated off and dried with magnesium sulfate, and the solvent was removed in vacuo. The residue (4.9 g of colorless oil) was submitted to column chromatography on (Merck) silica gel (70–230 mesh). Fractions 223–355 contained 2.05 g of a compound VIIIa as a colorless oil (72%).

Thin layer chromatogram (developer solution: toluene-ethyl acetate 4:1): R$_f$=0.18.

Nuclear magnetic resonance (in CDCl$_3$), δ-values: 1.2–1.9 multiplet 12H (—CH$_2$—), 1.9–2.8 multiplet 6H (—CH$_2$—, —CH—), 3.2–4.2 multiplet 8H (—OCH$_2$—, —OCH<), 4.5–4.7 multiplet 2 H (—O—CH—O—),
$\quad\quad\quad\quad\quad\quad\quad\quad\quad\quad\quad\quad$ |

4.7–5.2 multiplet 1H (—COO—CH—), 5.4–5.8 multiplet 2H (olefinic protons), 6.2–7.3 multiplet 3H (thiophene).

(b)

2-oxa-3-oxo-6-(3-tetrahydropyranyloxy-4-(2-thienylmethyloxy)-1-butenyl1)-7-tetrahydropyranyloxy-bicyclo(3.3.0)octane DC: Rf∼0.32, toluene/ethyl acetate 1:1
Nuclear magnetic resonance:

---
multiplet 1.2–1.9: 12 H (—CH$_2$—)
multiplet 1.9–2.8: 6 H (—CH$_2$—, CH)
multiplet 3.2–4.5: 8H (CH$_2$O, CHO)
multiplet 4.5–5.2: 5H (CH—O, OCH$_2$-thiophene,
$\quad\quad\quad\quad\quad\quad\quad\quad\quad\quad\quad\quad$ |
$\quad\quad\quad\quad\quad\quad\quad\quad\quad\quad\quad\quad$ O
$\quad\quad\quad\quad\quad\quad\quad\quad\quad\quad\quad\quad\quad$ O
$\quad\quad\quad\quad\quad\quad\quad\quad\quad\quad\quad\quad\quad$ ‖
—CH—O—C—)
multiplet 5.4–5.7: 2 olefinic H
multiplet 6.9–7.1 ppm $\}$ 3-thiophene-H
multiplet 7.2–7.4 ppm

---

EXAMPLE 6a

Synthesis of 2-oxa-3-hydroxy-6(3'-tetrahydropyranyloxy-4-(3-thienyl-oxy)-1-butenyl)-7-tetrahydropyranyloxy-bicyclo[3.3.0]octane IXa 2.0 g of the compound VIIIa were dissolved in 40 ml of toluene and were then cooled to −70° C. and 10.4 ml of a 1.2 M solution of diisobutyl-aluminum hydride in toluene was added dropwise over the course of 3 minutes under an atmosphere of argon. The mixture was stirred for a further 2 hours at −70° C. and excess hydrogenation reagent was then decomposed with 10 ml of methanol. The reaction product was extracted with ethyl acetate and semi-saturated sodium chloride. The organic phase was separated off and dried with magnesium sulfate and the solvent was removed in vacuo. The yield of the compound VIIIa was 1.9 g of a colorless oil (94.5%).

Thin layer chromatogram (developer solution: benzene-ethyl acetate 4:1): $R_f$=0.06.

Absorptions in the infrared spectrum (without solvent): 3,405 (OH-band), 2,935, no carbonyl band.

(b) 2-oxa-3-hydroxy-6(3-tetrahydropyranyloxy-4-(2-thienylmethyloxy)-1-butenyl)-7-tetrahydropyranyloxy-bicyclo(3.3.0)octane This compound was obtained in a 86% yield after preparation from 5b, according to Example 6a.
DC: Rf (toluene/ethyl acetate 1:1)~0.24.
IR-spectrum: OH-bands at 3400 (broad), no C=O bands.

EXAMPLE 7a

Synthesis of 9α-hydroxy-11α,15α-ditetrahydropyranyloxy-16-(3-thienyloxy)-5-cis-13-trans-tetranor-prostadienoic acid (Xa)

5 ml of absolute dimethylsulfoxide were added to 0.43 g of sodium hydride (80% strength suspension in oil) under argon and the mixture was stirred for 1 hour at 60° C. until the evolution of hydrogen ceases. After cooling to room temperature, this solution was treated dropwise with 3.34 g of 4-carboxybutyltriphenyl-phosphonium bromide (dried at 120° C. in a high vacuum) dissolved in 7 ml of absolute dimethylsulfoxide. Hereupon, the phosphonylide required for the Wittig reaction formed, and the mixture assumed an intense red coloration. The mixture was stirred additionally for 30 minutes at 30° C. 1.9 g of the compound IXa in 5 ml of dimethylsulfoxide were then added dropwise. The mixture was stirred for 2½ hours at room temperature and then added to ice water which was covered with diethyl ether. The neutral substances were extracted and the aqueous solution was acidified with 5% strength sodium bisulfate solution to pH 2, while cooling with ice, and was immediately extracted with ether. The ether solution was then extracted with 0.5 N sodium hydroxide solution and the aqueous alkaline layer was separated off and again acidified, while cooling with ice, and extracted with ether; the ether solution was dried with magnesium sulfate, filtered and concentrated in vacuo. The yield of the compound IXa, after column chromatography on 250 g of silica gel (solvent system: ethyl acetate-acetic acid, 97.5:2.5), was 1.3 g of a slightly yellow oil (57%).

Thin layer chromatogram (developer solution: ethyl acetate-acetic acid, 97.5:2.5), $R_f$=0.51.

Absorptions in the infrared spectrum (without solvent): 3,405 (OH-band), 2,950, 1,725 (carbonyl band).

(b) 9α-hydroxy-11α,15-bis-tetrahydropyranyloxy-16-(2-thienylmethyl-oxy)-5cis-13-trans-tetranorprostadienoic acid This compound was prepared in an analogous manner. DC: (ethyl acetate/glacial acetic acid 97.5:2.5) Rf~0.55.

EXAMPLE 8a

Synthesis of 9α,11α,15-trihydroxy-16-(3-thienyloxy)-5-cis-13-trans-tetranor-prostadienoic acid I

15-S and 15-R epimer 1.3 g of the compound Xa were dissolved in 1.3 ml of tetrahydrofurane, 9 ml of a mixture of acetic acid and water in the ratio 2:1 were then added and the mixture was stirred for 3 hours at 40° C. under argon. The solvents were removed by repeated concentration in vacuo in the presence of benzene. This gave a crude yield of Ia of 1.1 g (slightly yellow oil).

The subsequent column chromatography with ethyl acetate-acetic acid 97.5:2.5 (on 180 g of Merck silica gel (70–230 mesh)) gave the following (individual fractions: 4 ml):

156 mg of 15-R epimer
195 mg of 15-S epimer
Yield: 0.35 g (45.2%).

Thin layer chromatogram (solvent as for column chromatography):

| 15-R epimer | $R_f$ = 0.24 |
| --- | --- |
| 15-S epimer | $R_f$ = 0.18 |

Nuclear resonance spectra (in $CDCl_3$), δ-values: (the spectra for the 15-R epimer and the 15-S epimer were practically identical, within the scope of the customary resolution): 0.8–2.6 multiplet 12H (—CH$_2$—, —CH—), 3.5–4.8 multiplet 5H (—CH—OH) (—CH$_2$—O—), 5.2–5.8 multiplet 4H (olefinic protons), 5.8–6.2 broad singlet 4H (3×OH, 1×COOH), 6.2–7.3 multiplet 3H (thiophene).

The signal at 5.8–6.2 ppm can be removed by H/D exchange.

(b) 9α,11α,15-trihydroxy-16,16-dimethyl-16-(3-thienyloxy)-5-cis,13-trans-tetranor-prostadienoic acid Nuclear magnetic resonance (in $CDCl_3$) δ-values:

| | |
| --- | --- |
| 7.6–6.4 ppm | (3 H, thienyl-H) multiplet |
| 6.2–5.9 ppm | (4 H, 1 × COOH, 3 × OH) broad signal |
| 5.8–5.2 ppm | (4 H, olefinic protons) multiplet |
| 4.4–3.8 ppm | (3 H, CH—OH) multiplet |
| 2.7–1.4 ppm | (12 H, —CH$_2$—) multiplet |
| 1.35 ppm | (6 H, —CH$_3$)$_2$) singlet |

(c) 9α,11α,15-trihydroxy-16-(5-methyl-2-thienyloxy)-5-cis 13-trans-tetranor-prostadienoic acid Nuclear magnetic resonance (in $CDCl_3$) δ-values:

| | |
|---|---|
| multiplet at 6.2–6.4 ppm | (1 H, thiophene) |
| doublet at 6.0 ppm | (1 H, thiophene) |
| broad singlet at 5.7–5.9 ppm | (3 × OH, 1 × COOH) |
| multiplet at 5.2–5.8 ppm | (4 olefinic H) |
| multiplet at 3.3–4.5 ppm | (5 H, CH—OH, CH$_2$—O—) |
| doublet at 2.3 ppm | (3 H, CH$_3$, J = 1.5 Hz) |
| multiplet at 0.8–3.2 ppm | (12 H) |

(d)
9α,11α,15-trihydroxy-16-(2-thienylmethyloxy)-5-cis-13-trans-tetranor-prostadienoic acid Nuclear magnetic resonance (in CDCl$_3$) δ-values:

multiplet 7.6–7.0 ppm (7 H, 3 thiophene-H, 3 OH, 1 COOH)
multiplet 5.2–5.8 ppm (4 olefinic H)

singlet at 4.7 ppm (2 H, —OCH$_2$—⟨thienyl⟩)

multiplet 3.2 to 4.5 ppm (5 H, —CH—OH, CH$_2$O—)
multiplet 0.8 ppm–3.6 ppm (12 H)

(e)
9α,11α,15-trihydroxy-16-(3,5-dimethyl-2-thienyloxy)-5-cis-13-trans-tetranor-prostadienoic acid Nuclear magnetic resonance (in CDCl$_3$) δ-values:

| | |
|---|---|
| 6.15 ppm | 1 H, thienyl) |
| broad singlet 6.4–6.7 ppm | (3 × OH, 1 × COOH) |
| multiplet 5.2–5,8 ppm | (4 H, olefinic protons) |
| multiplet 3.3–4.4 ppm | (5 H, —CH—OH, —CH$_2$O—) |
| multiplet 1.1–3.5 ppm | (12 H) |
| doublet 2,28 ppm | (3 H, J < 1.5 Hz, CH$_3$) |
| singlet 2.0 ppm | (3 H, CH$_3$) |

(f)
9α,11α,15-trihydroxy-16-(cyclopentano[b]thienyl-3-oxy)-5-cis, 13-trans-tetranor-prostadienoic acid Nuclear magnetic resonance (in CDCl$_3$) δ-values:

| | |
|---|---|
| 6.1 singlet | (CH-thiophene) |
| 5.2–5.8 multiplet | (4 H, olefinic protons) |
| 5.0–5.3 broad singlet | (3 × OH, 1 × COOH, 4 H) |
| 3.4–4.5 multiplet | (5 H, CH—OH, CH$_2$O) |
| 1.2–3.3 multiplet | (18 H, —CH$_2$—, —CH—) |

(g)
α,11α,15-trihydroxy-16-(2-phenyl-thienyl-3-oxy)-5-cis, 13-trans-tetranor-prostadienoic acid Nuclear magnetic resonance (in CDCl$_3$) δ-values:

7.7–7.3 multiplet (phenylprotons, 5 H)
7.1 doublet (1 H, J = 2 Hz, thiophene)
6.1 doublet (1 H, J = 2 Hz, thiophene)
5.2–5.8 multiplet (4 H, olefinic protons)
4.9–5.1 broad singlet (3 × OH, 1 × COOH, 4 H)
3.2–4.5 multiplet (5 H, —CH—OH, CH$_2$—O)

1.1–3.2 multiplet (12 H, —CH$_2$—, —CH—)

(h)
9α,11α,15-trihydroxy-16-(2-methyl-3-thienyloxy)-5-cis 13-trans-tetranor-prostadienoic acid Nuclear magnetic resonance (in CDCl$_3$) δ-values:

7.0–6.5 multiplet (2 H, thiophene)
6.4–6.0 broad singlet (4 H, 3 × OH, 1 × COOH)
5.2–5.75 multiplet (4 H, olefinic protons)
3.3–4.3 multiplet (5 H, —CH—OH, —CH$_2$—O—)
2.3 singlet (3 H, CH$_3$)
1.2–3.15 multiplet (12 H, —CH$_2$—, —CH—)

(i)
9α,11α,15-trihydroxy-16-(3-methoxy-2-thienylmethyloxy)-5-cis, 13-trans-tetranor-prostadienoic acid Nuclear magnetic resonance (in CDCl$_3$) δ-values:

7.2–6.8 multiplet (2 H, thiophene)
6.2–6.4 broad singlet (4 H, 3 × OH, 1 × COOH)
5.15–5.8 multiplet (4 H, olefinic protons)
3.3–4.6 multiplet (7 H, —CH—OH, —OCH$_2$—)
3.8 singlet (3H, OCH$_3$)
1.2–3.2 multiplet (12 H, —CH$_2$—, —CH—)

What is claimed is:
1. A racemic compound, or an opbically active compound of natural configuration, of the formula

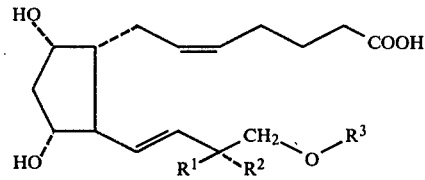

physiologically acceptable salts thereof with organic or inorganic bases, and esters thereof with aliphatic, cycloaliphatic, or araliphatic alcohols having up to 8 carbon atoms, wherein $R^1$ and $R^2$ each is hydrogen or hydroxy but $R^1$ and $R^2$ are different; and $R^3$ is α-thienyl, β-thienyl, or α-or β-thienyl mono-, di-, or tri-substituted by at least one member selected from the group consisting of chloro, trifluoromethyl, or methyl.

2. A pharmaceutical composition comprising a pharmaceutical carrier and a therapeutically-effective amount of a compound as in claim 1.

3. A method of treatment which comprises administering a therapeutically effective amount of a compound as in claim 1.

* * * * *